US011769302B2

(12) United States Patent
Olson et al.

(10) Patent No.: US 11,769,302 B2
(45) Date of Patent: Sep. 26, 2023

(54) REMOTE SURGICAL MENTORING

(71) Applicant: Verb Surgical Inc., Santa Clara, CA (US)

(72) Inventors: Blade Olson, Mountain View, CA (US); Bernhard A. Fuerst, Sunnyvale, CA (US)

(73) Assignee: Verb Surgical Inc., Santa Clara, CA (US)

(*) Notice: Subject to any disclaimer, the term of this patent is extended or adjusted under 35 U.S.C. 154(b) by 468 days.

(21) Appl. No.: 16/894,515

(22) Filed: Jun. 5, 2020

(65) Prior Publication Data

US 2021/0378768 A1     Dec. 9, 2021

(51) Int. Cl.

| | |
|---|---|
| *G06T 19/00* | (2011.01) |
| *A61B 34/35* | (2016.01) |
| *A61B 34/37* | (2016.01) |
| *G16H 40/67* | (2018.01) |
| *G02B 27/01* | (2006.01) |
| *G06F 3/01* | (2006.01) |
| *A61B 34/30* | (2016.01) |

(52) U.S. Cl.
CPC ............ *G06T 19/006* (2013.01); *A61B 34/35* (2016.02); *A61B 34/37* (2016.02); *G02B 27/017* (2013.01); *G06F 3/011* (2013.01); *G16H 40/67* (2018.01); *A61B 2034/301* (2016.02); *G06T 2210/41* (2013.01)

(58) Field of Classification Search
CPC . G06T 19/006; G06T 2210/41; G02B 27/017; G06F 3/011; G16H 40/67
See application file for complete search history.

(56) References Cited

U.S. PATENT DOCUMENTS

| | | | | |
|---|---|---|---|---|
| 2012/0249416 | A1* | 10/2012 | Maciocci | G06F 3/011 |
| | | | | 345/156 |
| 2017/0319282 | A1* | 11/2017 | Jarc | A61B 34/10 |
| 2019/0005848 | A1* | 1/2019 | Garcia Kilroy | G06T 3/20 |
| 2020/0121556 | A1* | 4/2020 | Tian | A61H 39/02 |
| 2020/0160607 | A1* | 5/2020 | Kjallstrom | G06T 19/006 |

(Continued)

FOREIGN PATENT DOCUMENTS

WO     2019005983     1/2019

OTHER PUBLICATIONS

International Search Report and Written Opinion for International Application No. PCT/US2020/038088 dated Mar. 4, 2021, 15 pages.

(Continued)

*Primary Examiner* — William A Beutel
(74) *Attorney, Agent, or Firm* — AIKIN & GALLANT, LLP (57) ABSTRACT

A virtual representation of an operating room is generated based on robot information and sensing of the OR with depth cameras. One of the depth cameras is integrated with a portable electronic device, operated by a local user in the operating room. The virtual representation of the OR is communicated to the virtual reality headset, with three-dimensional point cloud data. A virtual reality environment is rendered to a display of the virtual reality headset, operated by a remote user. A virtual representation of the remote user is rendered in augmented reality to a display of the portable electronic device.

20 Claims, 5 Drawing Sheets

OPERATING ROOM WITH AUGMENTED REALITY AND REMOTE USER (56) References Cited

U.S. PATENT DOCUMENTS

2020/0330166 A1* 10/2020 Meglan .............. A61B 17/3423
2021/0072947 A1*  3/2021 Anderson ............... G06F 3/011

OTHER PUBLICATIONS

Shenai, Mahesh B., et al., "Virtual Interactive Presence and Augmented Reality (VIPAR) for Remote Surgical Assistance," Operative Neurosurgery, vol. 68, No. 3, Mar. 1, 2011, 8 pages.
International Preliminary Report on Patentability for International Application No. PCT/US2020/038088 dated Dec. 15, 2022, 8 pages.

* cited by examiner

REMOTE SURGICAL MENTORING

TECHNICAL FIELD

This disclosure relates generally to the field of surgical robotics and, more particularly, to remote surgical mentoring.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one endoscopic camera through the incisions into the patient. The surgical procedures are then performed by using the introduced tools, with the visualization aid provided by the camera.

Generally, MIS provides multiple benefits, such as reduced patient scarring, less patient pain, shorter patient recovery periods, and lower medical treatment costs associated with patient recovery. In some embodiments, MIS may be performed with surgical robotic systems that include one or more robotic arms for manipulating surgical instruments based on commands from an operator. For example, an operator may provide commands for manipulating surgical instruments, while viewing an image that is provided by a camera and displayed on a display to the user.

Performance of a surgical procedure can require in-depth knowledge and experience regarding different aspects of the surgery, including setup, workflow, and more. The use of surgical robotic systems potentially increases the complexity of the surgery. It can be helpful for a surgeon or assistant to collaborate pre-operatively, intra-operatively, and post operatively, with remotely located medical professionals. Procedures can be improved upon, and risk can be identified and reduced, through remote collaboration.

SUMMARY

Generally, a surgical robotic system has remote mentoring features that allow for pre-operative, intraoperative, and post-operative collaboration. Remote mentoring features can provide an intuitive and robust method for guiding intraoperative procedures via a remote mentor. A remote user (a 'mentor') wears a virtual reality (VR) headset to orchestrate an avatar, which is a digital representation of the mentor, that is virtually introduced into the operating room and visible by a local user that is controlling or wearing an augmented reality (AR) device such as a computer tablet, mobile smartphone, or headset (e.g., augmented reality or mixed reality glasses). AR refers to superimposing virtual objects (e.g., a digital representation of the mentor) over a video feed showing the physical environment of the AR user, in this case, the operating room. The virtual objects are typically integrated into the physical environment of the user, for example, by being interactive with the physical environment. It should be understood that, for the purpose of this disclosure, the terms augmented reality and mixed reality are interchangeable.

The remote VR user and the local intraoperative AR user are both bounded in a shared coordinate frame relative to the Verb robotic system. In other words, they have a common coordinate system so that they are co-located in the same virtual space in a realistic manner. The remote virtual reality user is visible not only through the avatar, but can also create notes and markings that are localized within 3D space, provide recommendations and examples for robotic arm movement/positions, and recommend surgical table orientation/position. Audio streams of the remote and local user can be transmitted back and forth between the remote and local users, to facilitate verbal communication. Thus, inputs (e.g., the notes, markings, recommendations, and/or audio) from the remote user can provide the local user with helpful insight regarding different aspects of a surgical procedure.

In turn, the point cloud information of the physical operating room environment can be captured by depth cameras and transmitted back to the virtual reality environment for the remote user to view and manipulate. By using an augmented reality headset/tablet as a sensor source and data generator, the remote VR user can construct a 3D mesh of the patient in VR that will instruct and enable intraoperative guidance.

In some embodiments, the system can include a plurality of depth cameras (e.g., RGBD scanners or equivalent technology). At least one of the depth cameras is integrated with a portable electronic device operated by a local user in an operating room (OR). Another one of the depth cameras is arranged in the OR, such as being mounted on equipment and/or walls. The system can include a surgical robot, such as robot arms and platform for supporting a patient during surgery, and controller for commanding movements of the surgical robot.

A virtual representation of the OR is generated based on a) robot information received from the surgical robot or controller, and b) sensing of the OR by the plurality of depth cameras. The virtual representation of the OR and three dimensional point cloud data is transmitted to a virtual reality headset used to render a virtual reality environment to a display of the virtual reality headset worn by a remote user. In this manner, a remote user can 'see' what is happening in the OR and provide insight.

A virtual representation of the remote user is rendered in augmented reality at the portable electronic device. The virtual representation can be a graphical object superimposed over a 'live' video feed of the OR. The virtual representation of the remote user can be generated based on position of the remote user, such that the virtual representation of the remote user shares a common coordinate system that is common to the virtual representation of the OR, the surgical robot, and the portable electronic device of the local user. In other words, if the remote user moves forward towards the patient in the virtual representation of the OR (as shown to the remote user in the virtual reality headset), the avatar of the remote user will simultaneously move forward towards the patient as shown in the augmented reality displayed to the local user. Similarly, if the remote user 'points' at a section of the patient in the virtual reality environment that is shown to the remote user, the avatar of the remote user will point at the corresponding section of the patient in the augmented reality shown to the local user. This creates a 'realistic' interaction between the local and remote user and merges the augmented reality of the local user with the virtual reality of the remote user.

Inputs from the remote user such as audio data (e.g., the remote user's speech) and virtual annotations generated by a digital tool (e.g., handheld user input device held by the remote user) can be indicated through the virtual representation of the remote user. The virtual representation can be a simplified rendering of a person (e.g., a head and hands), a realistic representation, or a symbolic representation, that communicates the remote user's gestures, movements, position, and/or intention to the user.

DETAILED DESCRIPTION

Non-limiting examples of various aspects and variations of the invention are described herein and illustrated in the accompanying drawings.

Figure 1:
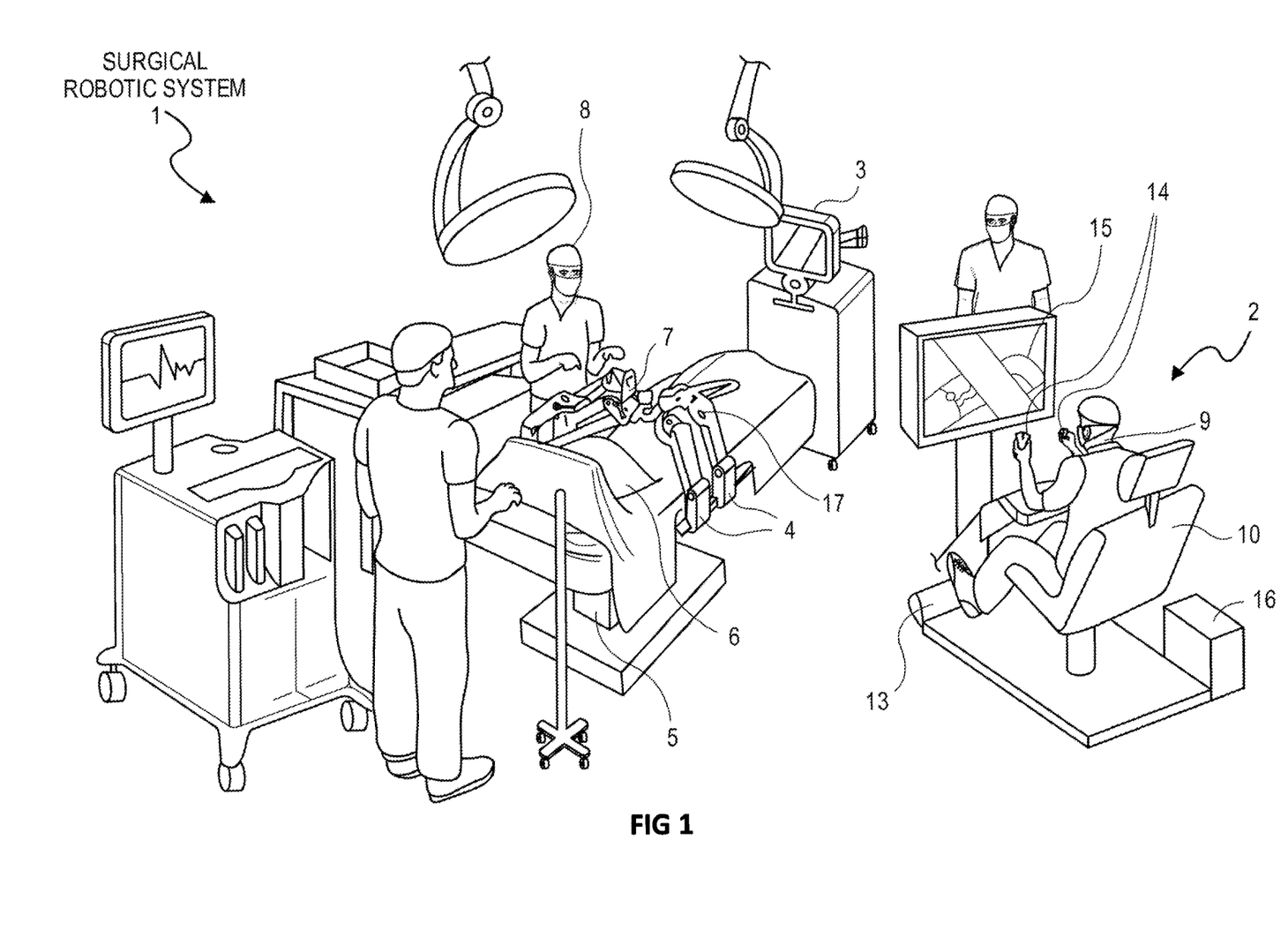
FIG. 1 shows an example of a surgical robotic system in an operating room according to some embodiments.

Referring to FIG. 1, this is a pictorial view of an example surgical robotic system 1 in an operating arena. The system 1 includes a user console 2, a control tower 3, and one or more surgical robotic arms 4 at a surgical robotic platform 5, e.g., a table, a bed, etc. The arms 4 may be mounted to a table or bed on which the patient rests as shown in the example of FIG. 1, or they may be mounted to a cart separate from the table or bed. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In one aspect, the surgical tool 7 is a grasper that can grasp tissue of the patient. The surgical tool 7 may be configured to be controlled manually by a bedside operator 8, robotically via actuated movement of the surgical robotic arm 4 to which it is attached, or both. The robotic arms 4 are shown as being table-mounted but in other configurations the arms 4 may be mounted to a cart, the ceiling or a sidewall, or to another suitable structural support.

A remote operator 9, such as a surgeon or other human operator, may use the user console 2 to remotely manipulate the arms 4 and their attached surgical tools 7, e.g., referred to here as teleoperation. The user console 2 may be located in the same operating room as the rest of the system 1 as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 that are mounted on the distal ends of the arms 4.

In some variations, the bedside operator 8 may operate the system 1 in an "over the bed" mode in which the beside operator 8 (user) is at a side of the patient 6 and is simultaneously manipulating a robotically-driven tool (an end effector that is attached to the arm 4) with a handheld UID 14 held in one hand, and a manual laparoscopic tool in another hand. For example, the bedside operator's left hand may be manipulating the handheld UID to control a robotically-driven tool, while the bedside operator's right hand may be manipulating a manual laparoscopic tool. In this particular variation of the system 1, the bedside operator 8 can perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g. position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, which opens or closes jaws of the grasper at a distal end of surgical tool 7 to grip tissue within patient 6.

In some aspects, the communication between the platform 5 and the user console 2 may be through a control tower 3, which may translate user commands that are received from the user console 2 (and more particularly from the console computer system 16) into robotic control commands that transmitted to the arms 4 on the robotic platform 5. The control tower 3 may also transmit status and feedback from the platform 5 back to the user console 2. The communication connections between the robotic platform 5, the user console 2, and the control tower 3 may be via wired and/or wireless links, using any suitable ones of a variety of data communication protocols. Any wired connections may be optionally built into the floor and/or walls or ceiling of the operating room. The robotic system 1 may provide video output to one or more displays, including displays within the operating room as well as remote displays that are accessible via the Internet or other networks. The video output (video feed) may also be encrypted to ensure privacy and all or portions of the video output may be saved to a server or electronic healthcare record system.

Figure 2:
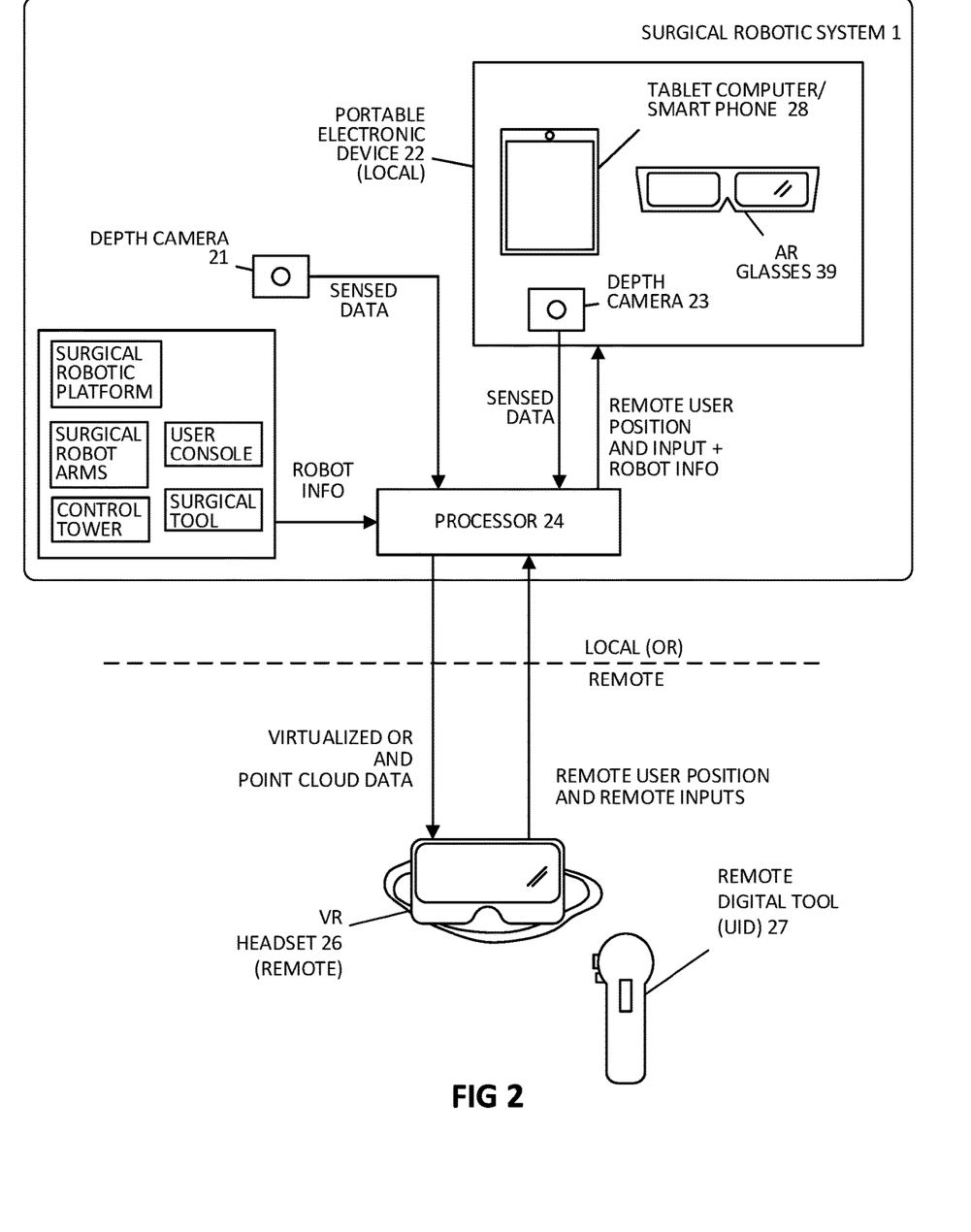
FIG. 2 shows a surgical robotic system with remote telementoring features according to some embodiments.

FIG. 2 shows the surgical robotic system 1 having remote features that allow surgeons to collaborate pre-operatively, intra-operatively, and post-operatively. The development of a real-time virtual reality and augmented reality collaboration platform enables an interaction paradigm in which a remote surgical professional can conveniently observe and advise surgeries from disparate locations.

A processor 24 can generate a virtual representation of an operating room based on a) robot information, and b) sensing of the operating room by one or more depth cameras (e.g., cameras 21, 23). The depth cameras can include at least one depth camera 23 integrated with a portable electronic device 22 operated by a local user in the operating room, and at least one stationary depth camera 21 arranged in the operating room at a fixed location (e.g., on walls and/or on equipment). The depth cameras can be RGBD sensors, or other equivalent technology that senses color and depth.

The robot information is generated by components of the surgical robotic system shown in FIG. 1. For example, the surgical robotic platform can provide telemetry generated by servos or sensors that indicates position and orientation (e.g., platform height and angle) at which the platform is currently held at. Similarly, sensors or controllers of the surgical robot arms and surgical tool can provide telemetry that describes the position (e.g., joint angles) of the surgical robotic arms, tool types that are currently attached to the robotic arms, tool grasp status (e.g., 90% closed), and active tool energy. This data can be collected at the control tower or user console. Further, system information such as system state (on, off, idle) or error code can be collected and shared with a remote user.

The processor can use the robot information to generate a virtual representation of the respective robotic components in the positions indicated by the robot information based on, for example, the robotic joint angles and the platform height and angle. This can obviate the need to extrapolate precise positioning of the platform, robotic arms and tools from image data sensed by the depth cameras, while also improving accuracy of the virtual representation of these components, which is included in the virtual representation of the operating room.

In some embodiments, the portable electronic device 22 can be a tablet computer or mobile smartphone 28. Augmented reality (e.g., the representation of remote user and/or other virtual objects) is rendered on the display of the device, superimposed over a stream of images captured by the device. Alternatively, the portable electronic device can be a head worn device such as augmented reality or mixed reality glasses 39, having a transparent display worn in front of eyes, onto which the augmented reality is rendered over. This is done in 'real-time' or 'live', meaning that the processing and display of the augmented reality is performed contemporaneous with the capturing of the stream of images, notwithstanding unavoidable delays such as buffering, processing, and communication latency.

A virtual representation of the operating room and three dimensional point cloud data is transmitted to a virtual reality headset 26 (operated by a remote user) used to render a virtual reality environment to a display of the virtual reality headset. The virtual reality environment here is fully immersive, meaning that the content shown to the remote user is not integrated with the remote user's environment, rather the remote user is virtually transported to the operating room.

The virtual representation of the operating room can include a three-dimensional rendering of the operating room and components in the operating room. In some cases, the virtualized operating room can include metadata such as equipment type, location and orientation, so that the virtual reality headset can render those objects into the virtual reality environment, thus reducing the amount of data that must be transmitted to the virtual reality headset, for example, if raw 3D point cloud data for all objects of the environment was to be transmitted. The virtual representation of the operating room can include mesh representations of objects, walls, ceiling, personnel (e.g., surgeons, assistants, etc.) that are sensed in the OR environment. The virtual representation of the operating room can be constructed based on 3D point cloud data that is captured by the plurality of depth cameras.

The virtual representation can be generated by processor 24. The processor can be integral to a standalone computer, integrated with the controller, a laptop, the portable electronic device that is operated by the local user, or other computing systems of the surgical robotic system.

It is recognized, however, that for some areas, it is beneficial to transmit raw 3D point cloud data to the remote user, to provide greater detail and resolution, and to allow the remote user greater ability to interact with the sensed environment of the operating room. This 3D point cloud data can be generated by the depth camera of the portable electronic device 22, or by one or more depth cameras mounted in the OR on equipment or walls, directed at an area of interest. For example, the local user can aim the depth camera 23 of the portable electronic device at areas of interest on a patient (e.g., at a patient abdomen). This raw 3D point cloud data can be transmitted to the remote VR headset to allow the remote user to analyze and manipulate this raw image data.

For example, remote surgeons can perform segmentation of organs on a patient as another surgeon is performing a surgery so that intraoperative personnel can receive real-time visual guidance on physiological landmarks. Segmentation refers to the process of dividing an image into regions with similar properties such as gray level, color, texture, brightness, and contrast. Thus, the remote user can subdivide objects in the image to help identify regions of interest (e.g., parts of organs, tumors, lesions, other abnormalities). Based on the raw point cloud data, the remote user can also identify locations on a patient for ports that serve as entry points for the surgical robotic instruments. Thus, having a depth camera that can be directed to areas of interest allows the local user to send detailed scans of the patient to the remote user.

The processor uses the robot information and the sensor data sensed by the depth cameras to recognize and virtually establish the 3D position and orientation of the surgical robotic system and its components in the AR device's coordinate frame. This can be performed through known computer vision algorithms, such as image classification and object localization, and performing transformations from one coordinate system to another to determine a common coordinate system.

Through this process, the depth cameras arranged across surgical robotic system and the portable electronic device establish a common coordinate frame and create a virtual recreation of the robotic arms/table that matches the real-time position/orientation of the robotic arms/table in the room. After the components of the surgical robotic system are localized in 3D space (e.g. the control tower, surgeon bridge, and table and arms), a remote participant can interact with a virtual reconstruction of the OR. The virtual representation of the remote user (e.g., orientation/position of the remote user's hands, body, and/or head) is communicated to the augmented reality user in the same relative coordinate frame.

A simultaneous localization and mapping (SLAM) algorithm is performed upon data generated by the at least one depth camera integrated with the portable electronic device, to localize the position and orientation of the portable electronic device 3D space and in the common coordinate system.

The portable electronic device of the local user and/or the processor 24 can have a data connection to the surgical robotic system so that it can retrieve real-time robot information (e.g., the robot's arm joint angles, tool types, tool grasp status, active tool energy, arm modes, table position and orientation, the case surgeon, and troubleshooting error codes). This can be used to generate the virtual OR, and provide notifications to the local user and remote user.

In addition to localizing the components (e.g., the platform, user console, control tower, robotic arms) of the surgical robotic system in 3D space, the remote user is sent a live "window" into the 3D intraoperative space through a 3D point-cloud stream that is generated by the one or more depth cameras (e.g., 23 and/or 21). This point cloud provides a real-time stream of actual depth and RGB data from the OR, rather than a simplified stream of component position/orientation data that adjusts pre-rendered components of the surgical robotic system and OR components in the remote user's virtual reality environment. This point cloud stream, displayed in the correct coordinate space relative to the rest of the virtual reality environment, unlocks additional capabilities of the remote user.

Figure 3:
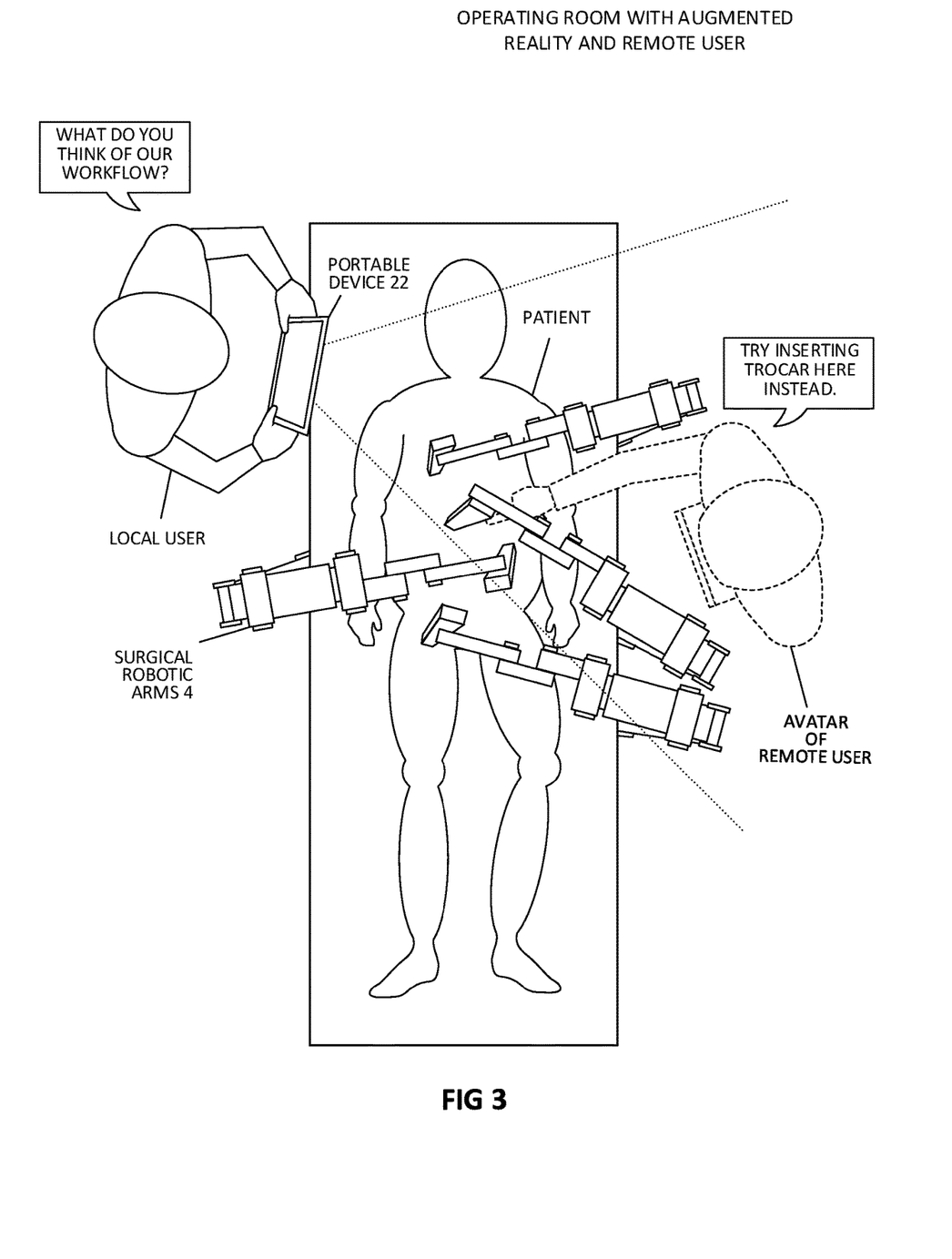
FIG. 3 illustrates a remote user being virtually imported into an operating room in an augmented reality experience, according to some embodiments.
Figure 4:
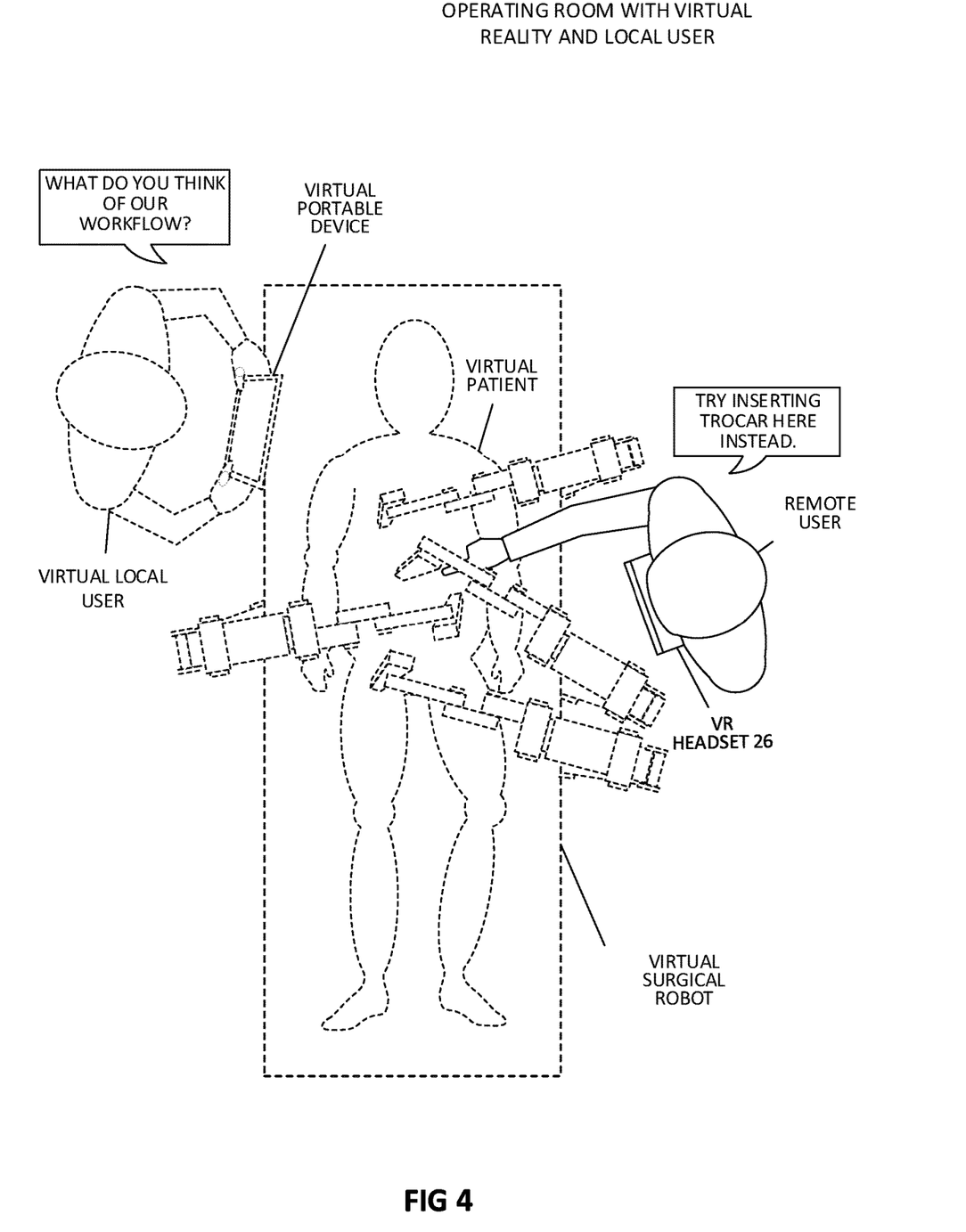
FIG. 4 illustrates an operating room and local user being virtually imported into a virtual reality experience of a remote user, according to some embodiments.

For example, the remote user can see the patient's body in greater detail through the 3D point cloud data (or a mesh generated based on the 3D point cloud data), and create digital waypoints and virtual guides for where trocars should be placed in a patient (see, for example, FIG. 4). Additionally, or alternatively, the remote user can create digital waypoints and virtual guides for how the robotic arms should be oriented relative to the patient's body. Additionally, or alternatively, the remote user can give educated advice about where staff should be standing in the operating room, or where equipment should be arranged in the operating room. The local user interacts with the remote user through the portable device 22, as shown in FIG. 3.

FIG. 3 illustrates the operating room and a virtual representation of the remote user placed in the operating room, creating an augmented reality experience for the local user. A virtual representation of the remote user is rendered in augmented reality to a display of the portable electronic device 22 based on position of and input from, the remote user. The position of the remote user shares a common coordinate system, i.e. it is common to the virtual representation of the OR, and the portable electronic device of the local user.

The position of the remote user, relative to the OR, can be determined using one or more points of reference at the user's remote location. For example, at the remote location of the remote user, sensors can be arranged in the surroundings of the remote user, and/or on the VR headset. A point of origin can be selected (e.g., arbitrarily) in the remote user's location to match a point of origin in the space of the operating room. Transformations can be performed to map movement and location of the remote user to the virtual representation of the OR. Thus, location and orientation of the remote user can be calculated in relation to the coordinate system of the operating room, allowing the remote user to virtually explore and interact with the operating room.

As discussed in other sections, the local user can aim a depth camera, which can be integrated with the portable device 22, at a location of interest, such as the patient's abdomen. Raw point cloud data generated by the depth camera can be transmitted in real-time to the remote user. Virtual markings and objects can be rendered over the display of the portable device, based on input generated by the remote user, such as: virtual annotations generated by a digital tool remotely, anatomical segmentation data, indications of trocar placement, and previous surgical set up.

For example, a remote user can use a handheld digital tool 27 as shown in FIG. 2 to circle areas to cut or remove, to mark where a port of entry for a trocar should be, or to mark where a suture is needed. These 'marks' can be virtually represented by virtual objects (e.g., lines, highlighted areas, or shapes) in the local user's portable device.

As discussed, input from the remote user can include audio data captured at the VR headset. Audio from the local user can simultaneously be transmitted to the VR headset, providing a two-way communication. Voice over IP (VOIP) or other audio communication technology can be used.

Referring back to FIG. 3, the local user can 'see' and 'hear' the remote user as the remote user verbally instructs and marks a location for where a trocar should be inserted. The virtual presence of the remote user creates a natural telementoring platform. Spatially contextual 3D markings and notes are communicated from the remote user to the local user. This can be contemporaneous with performance of a surgery. The remote user can provide visual guidance not only in the endoscope feed, but also around the robot, for example, how to orient arms, where to place endoscope and tools, where a 1st assistant should stand. The virtual representation of the remote user can include one or more of the following: a) a virtual representation of the virtual reality headset, b) virtual hands indicating hand movement or hand location of the remote user, and c) a virtual avatar resembling part of or a whole human.

FIG. 4 shows a virtual reality experience of the remote user. The remote user is transported to the operating room where the surgical robotic system is located. The remote user, wearing the VR headset 26, can explore the virtual space and provide inputs verbally and/or using a remote digital tool such as a digital pen or a handheld UID (e.g., remote digital tool 27 shown in FIG. 2).

The virtualized OR data and the point cloud data is communicated to the VR headset where it is used to render the virtual representation of the OR, and detailed areas of points of interest (e.g., the patient) onto a display of the remote user's VR headset. In addition, the position and orientation of the portable electronic device 22 of the local user can be communicated to the virtual reality headset. This can be used to render a virtual representation of the portable electronic device (e.g., floating in the virtual environment) and/or a virtual representation of the local user (e.g., an avatar) in the virtual reality environment. In this manner, the remote user can feel like she is interacting with the local user in the virtual OR.

As discussed in other sections, the remote user can use medical imaging segmentation to highlight, segment, and visually annotate tissues and organs that are relevant to the operation as the operation is proceeding. The remote user can load and overlay their own, previous surgical setups onto the augmented reality user's existing intraoperative setup as a guide for how they can organize their own OR/robot.

Figure 5:
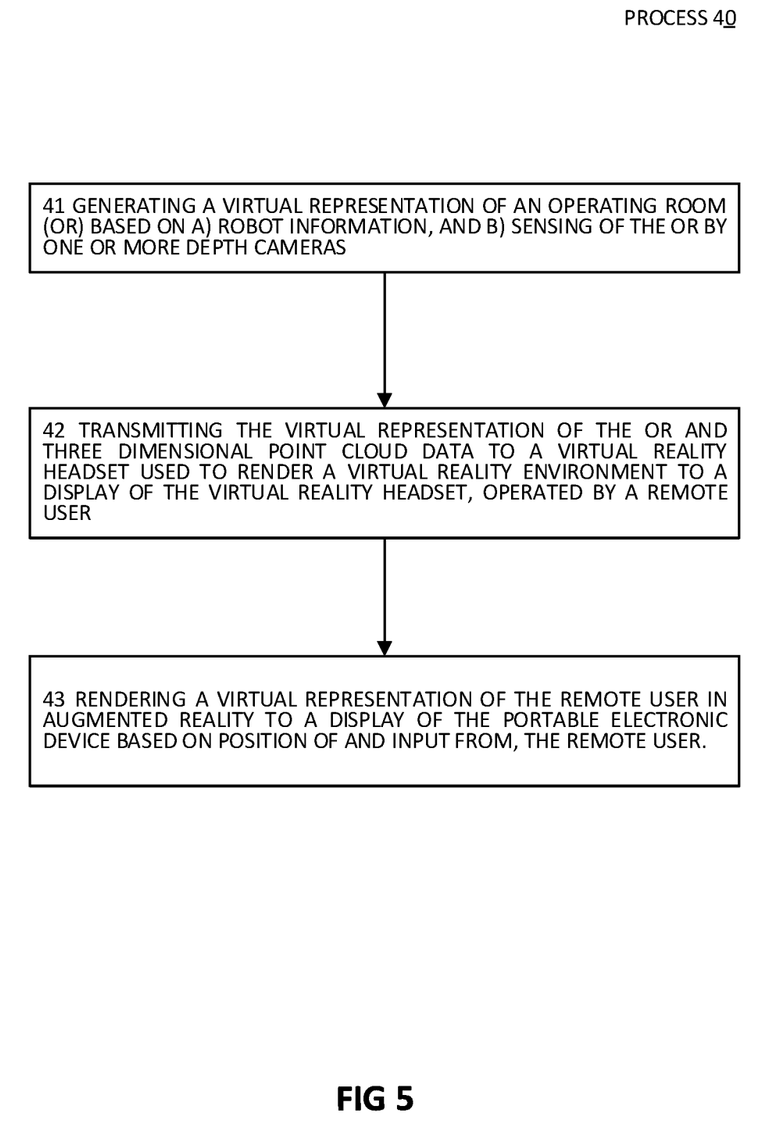
FIG. 5 shows a method for remote mentoring with a surgical robotic system, according to some embodiments.

A method 40 is shown in FIG. 5 that provides interactive and immersive remote mentoring, according to some embodiments. The method can be performed by the surgical robotic system shown in FIG. 1 and FIG. 2. For example, the method can be performed by processor 24, which can be integral to a standalone computer, integrated with components of the surgical robotic system 1 (shown in FIG. 1 or FIG. 2), or integrated with the portable electronic device 22 of FIG. 2.

At operation 41, the method includes generating a virtual representation of an OR based on a) robot information, and b) sensing of the OR by one or more depth cameras. The depth cameras include at least one depth camera integrated with a portable electronic device operated by a local user in the OR, and at least one stationary depth camera arranged in the OR. The robot information can be used to more accurately generate positions of the robotic components such as the robot arms, tools/instruments attached thereto, and the surgical platform.

At operation 42, the method includes transmitting the virtual representation of the OR and three dimensional point cloud data to a virtual reality headset where this is used to render a virtual reality environment to a display of the virtual reality headset, operated by a remote user. The virtual representation of the OR can include mesh data describing geometry of the operating room and objects in the room, and/or position and orientation data of recognized objects in the operating room. The remote user is virtually transported into the operating room, so that the remote user can analyze the setup, workflow, or provide other helpful insights to perform a surgery.

At operation 43, the method includes rendering a virtual representation of the remote user in augmented reality to a display of the portable electronic device based on position of and input from, the remote user. The virtual representation of the remote user is rendered in a common coordinate system that is common to the virtual representation of the OR, and the portable electronic device of the local user. The common coordinate system can be determined based on transformations between image data captured by a depth camera attached to or integrated with the portable electronic device, and image data captured by depth cameras mounted in the operating room.

The method can be performed continuously and in real-time. For example, operation 42 and operation 43 are performed continuously and simultaneously to provide a cohesive interaction between the local user and the remote user.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, and they thereby enable others skilled in the art to best utilize the invention and various embodiments with various modifications as are suited to the particular use contemplated.

What is claimed is:

1. A method for remote mentoring with a surgical robotic system, comprising:
receiving, during a surgical robotic procedure of a patient within an operating room (OR), 1) surgical robotic information that indicates a position of a surgical robotic arm in the OR and 2) sensor data captured by a first depth camera integrated within a portable electronic device operated by a local user in the OR and by a second depth camera arranged within the OR;
generating, using the surgical robotic information and the sensor data, a virtual OR that includes a virtual patient and a virtual surgical robotic arm;
generating three-dimensional (3D) point cloud data based on the sensor data, the 3D point cloud data representing at least a portion of the OR that includes the patient and the surgical robotic arm:
transmitting the virtual OR and the 3D point cloud data to a virtual reality headset used to render a virtual reality environment to a display of the virtual reality headset, operated by a remote user;
receiving input from the remote user indicating one or more recommended surgical ports of entry on the patient and a position of a virtual remote user within the virtual OR, wherein the position of the virtual remote user shares a common coordinate system that is common to 1) positions of the virtual patient and the virtual surgical robotic arm within the virtual OR and 2) a position of the portable electronic device within the OR; and
rendering, in augmented reality, the one or more recommended surgical ports of entry over the patient and the virtual remote user at the position within the virtual OR to a display of the portable electronic device.

2. The method of claim 1, wherein the augmented reality is rendered on the display over a stream of images of the OR that include the patient and the surgical robotic arm captured by the portable device such that the display shows the virtual remote user, the patient, and the surgical robotic arm in a shared space within the OR.

3. The method of claim 1, wherein the input from the remote user includes audio data captured at the virtual reality headset.

4. The method of claim 1, wherein the input from the remote user includes at least one of: virtual annotations generated by a digital tool remotely, anatomical segmentation data, trocar placement, and previous surgical set up, to be rendered in the augmented reality at the portable electronic device.

5. The method of claim 1, wherein the portable electronic device of the local user is a tablet computer and the augmented reality is rendered on the display over a stream of images captured by the tablet computer.

6. The method of claim 1, wherein the portable electronic device of the local user is a head worn device with a transparent display worn in front of eyes, onto which the augmented reality is rendered over.

7. The method of claim 1, wherein the robot information includes at least one of: joint angles of one or more surgical robotic arms, tool types, tool grasp status, active tool energy, position and orientation of a surgical table, and an error code of the surgical robotic system.

8. The method of claim 1, wherein simultaneous localization and mapping (SLAM) is performed upon data generated by the at least one depth camera integrated with the portable electronic device, to localize the position and orientation of the portable electronic device within the common coordinate system.

9. The method of claim 1, wherein the position and orientation of the portable electronic device is communicated to the virtual reality headset, used to render a virtual representation of the portable electronic device or a virtual representation of the local user in the virtual reality environment of the remote user.

10. The method of claim 1, wherein the one or more depth cameras include RGBD cameras.

11. The method of claim 1, wherein the virtual remote user includes at least one of: a) a virtual representation of the virtual reality headset, b) virtual hands indicating hand movement or hand location of the remote user, or c) a virtual avatar resembling part of or a whole human.

12. A surgical robotic system, comprising:
a plurality of depth cameras, including a depth camera integrated with a portable electronic device operated by a local user in an operating room (OR), and a stationary depth camera arranged in the OR;
a surgical robot and controller; and
a processor, configured to perform the following:
receiving, during a surgical robotic procedure of a patient in the OR, 1) surgical robotic information that indicates a position of the surgical robot in the OR and 2) sensor data captured by the depth camera and by the stationary depth camera;
generating, using the surgical robotic information and sensor data, a virtual OR that includes a virtual patient and a virtual surgical robot;
generating three-dimensional (3D) point cloud data based on the sensor data, the 3D point cloud data representing at least a portion of the OR that includes the patient and the surgical robot
transmitting the virtual OR and the 3D point cloud data to a virtual reality headset worn by a remote user, causing the virtual reality headset to render a virtual reality environment to a display of the virtual reality headset worn by the remote user; and
transmitting, to the portable electronic device of the local user and from the remote user, input indicating one or more recommended surgical ports of entry on the patient and a position of a virtual remote user within the virtual OR, wherein the position of the virtual remote user shares a common coordinate system that is common to 1) positions of the virtual patient and the virtual surgical robot within the virtual OR and 2) a position of the portable electronic device within the OR,
wherein the portable device of the local user is to render, in augmented reality, the received one or more recommended surgical ports of entry over the patient and the a virtual representation of the remote user at the position within the virtual OR.

13. The surgical robotic system of claim 12, wherein the augmented reality is rendered on the display over a stream of images of the OR that include the patient and the surgical robot captured by the portable device such that the display shows the virtual remote user, the patient, and the surgical robot in a shared space within the OR.

14. The surgical robotic system of claim 12, wherein the positions of the virtual patient and the virtual surgical robot within the virtual OR match positions of the patient and surgical robot within the OR, respectively, in the common coordinate system.

15. The surgical robotic system of claim 12, wherein the input from the remote user includes at least one of: virtual annotations generated by a digital tool remotely, anatomical segmentation data, trocar placement, and previous surgical set up, to be rendered in the augmented reality at the portable electronic device.

16. The surgical robotic system of claim 12, wherein the portable electronic device of the local user is a tablet computer and the augmented reality is rendered over a stream of images captured by the tablet computer and displayed on a screen of the tablet computer.

17. The surgical robotic system of claim 12, wherein the portable electronic device of the local user is a head worn display with a transparent display area onto which the augmented reality is rendered over.

18. The surgical robotic system of claim 12, wherein the robot information includes at least one of: joint angles of one or more surgical robotic arms, tool types, tool grasp status, active tool energy, position and orientation of a surgical table, and an error code of the surgical robotic system.

19. The surgical robotic system of claim 12, wherein simultaneous localization and mapping (SLAM) is performed upon data generated by the at least one depth camera integrated with the portable electronic device, to localize the position and orientation of the portable electronic device within the common coordinate system.

20. The surgical robotic system of claim 12, wherein the position and orientation of the portable electronic device is communicated to the virtual reality headset, used to render a virtual representation of the portable electronic device or a virtual representation of the local user in the virtual reality environment of the remote user.

* * * * *

UNITED STATES PATENT AND TRADEMARK OFFICE
CERTIFICATE OF CORRECTION

| | |
|---|---|
| PATENT NO. | : 11,769,302 B2 |
| APPLICATION NO. | : 16/894515 |
| DATED | : September 26, 2023 |
| INVENTOR(S) | : Blade Olson and Bernhard A. Fuerst |

It is certified that error appears in the above-identified patent and that said Letters Patent is hereby corrected as shown below:

In the Claims

Column 12,
Line 17, Claim 12, delete "a"

Column 12,
Line 17, Claim 12, delete "representation of the"

Signed and Sealed this
Fifteenth Day of October, 2024

Katherine Kelly Vidal
*Director of the United States Patent and Trademark Office*